United States Patent [19]

Sun

[11] 4,177,211

[45] Dec. 4, 1979

[54] PROCESS FOR THE PREPARATION OF BIS(AMINOPHENYL)ALKANES

[75] Inventor: Kwok K. Sun, Hamden, Conn.

[73] Assignee: The Upjohn Company, Kalamazoo, Mich.

[21] Appl. No.: 898,646

[22] Filed: Apr. 21, 1978

[51] Int. Cl.$^2$ ............................................. C07C 85/02
[52] U.S. Cl. .............................. 260/570 D; 260/345.5; 568/640
[58] Field of Search ......................... 260/570 D, 345.5

[56] References Cited

U.S. PATENT DOCUMENTS 3,418,371   12/1968   Krimm et al. ................... 260/570

*Primary Examiner*—Robert V. Hines
*Attorney, Agent, or Firm*—Denis A. Firth; John Kekich

[57] ABSTRACT

An improved process is described for the preparation of bis(aminophenyl)alkanes which comprises heating the corresponding bis(di-alkoxyphenyl)alkane or corresponding cyclic ethers of bis(phenyl)alkanes with an at least stoichiometric proportion of an aniline acid addition salt, optionally in the presence of an inert organic solvent.

15 Claims, No Drawings

PROCESS FOR THE PREPARATION OF BIS(AMINOPHENYL)ALKANES

BACKGROUND OF THE INVENTION

1. Field of the Invention

This invention relates to a process for the preparation of substituted diphenylalkanes and is more particularly concerned with an improved synthesis of di(aminophenyl)alkanes from the corresponding di(dialkoxyphenyl)alkanes.

2. Description of the Prior Art

Various methods are known for the preparation of 2,2-bis(4-aminophenyl)propane and like bis(aminophenyl)-alkanes. Illustratively, the former has been prepared by the condensation of acetone and aniline hydrochloride; see U.S. Pat. No. 3,670,024. An earlier process for the same compound involved the reaction of acetone and aniline under pressure in the presence of hydrochloric acid to yield the diamine in question in low yield; see U.S. Pat. No. 2,794,822. 2,2-Bis(4-aminophenyl)propane has also been prepared by direct amination of bisphenol A (see U.S. Pat. No. 3,860,650) and, as a by-product in low yield, by the reaction of bisphenol A with aniline (see U.S. Pat. No. 3,418,371). The main product of the latter reaction is 2-(4-hydroxyphenyl)-2-(4-aminophenyl)propane.

I have now found that 2,2-bis(4-aminophenyl)propane and related compounds can be obtained in high yield by an improved process which will be described below.

SUMMARY OF THE INVENTION

This invention comprises a process for the preparation of a bis(aminophenyl)alkane having the formula:

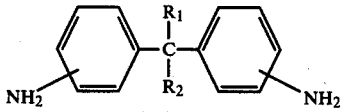

wherein $R_1$ and $R_2$, taken individually, represent methyl and lower-alkyl, respectively, and $R_1$ and $R_2$ taken together with the C atom to which they are attached represent the residue of a 1,1-cycloalkylidene group having from 5 to 7 ring carbon atoms, inclusive; said process comprising reacting (a) the appropriately substituted bis(phenyl)alkane having the formula:

wherein $R_1$ and $R_2$ have the significance defined above and A is a member selected from the class consisting of

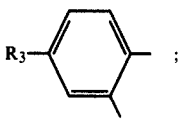

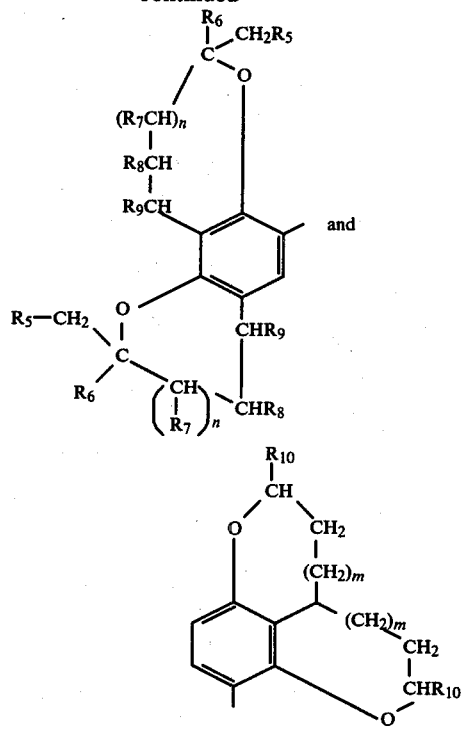

wherein $R_3$ and $R_4$ each represent lower alkoxy; $R_5$, $R_6$, $R_7$, $R_8$, $R_9$, and $R_{10}$ are each independently selected from the group consisting of hydrogen and lower-alkyl; and n and m are integers from 0 to 1; with (b) at least 2 moles, per mole of said bis(phenyl)alkane, of an aniline acid addition salt at a temperature in the range of 100° C. to 250° C.

The term "lower-alkyl" means alkyl from 1 to 8 carbon atoms, inclusive, such as methyl, ethyl, propyl, butyl, pentyl, hexyl, heptyl, octyl and isomeric forms thereof. The term "lower-alkoxy" means alkoxy from 1 to 8 carbon atoms, inclusive, such as methoxy, ethoxy, propoxy, butoxy, pentyloxy, hexyloxy, heptyloxy, octyloxy and isomeric forms thereof. The term "1,1-cycloalkylidene having from 5 to 7 ring carbon atoms, inclusive," means 1,1-cyclopentylidene, 1,1-cyclohexylidene, 1,1-cycloheptylidene, 2-methyl-1,1-cyclohexylidene, 2,2-dimethyl-1,1-cyclopentylidene, and the like alkyl-substituted 1,1-cycloalkylidenes.

The term "aniline acid addition salt" means a salt of aniline with a mineral acid such as hydrochloric, hydrobromic, hydrofluoric, sulfuric and phosphoric acids.

The bis(aminophenyl)alkanes of formula (I) which are produced in accordance with this invention are well-known compounds which are useful as curing agents for epoxy resins, as chain extenders in the preparation of polyurethanes and as monomers which can be converted by reaction with dicarboxylic acid halides to form polyamides and, by reaction with dicarboxylic acid anhydrides, to form polyimides using processes well-known in the art for the preparation of polyamides and polyimides from diamines. The bis(aminophenyl)alkanes of formula (I) can also be converted, by phosgenation using procedures conventional in the art, to the corresponding diisocyanates which can then be employed in the preparation of polyurethanes and like isocyanate-based polymers.

DETAILED DESCRIPTION OF THE INVENTION

In carrying out the process of the invention the substituted bis(phenyl)alkane of formula (II) and the aniline acid addition salt are brought together in any appropriate manner and heated at a temperature in the range of about 100° C. to about 250° C., preferably in the range of about 180° C. to about 220° C., until the desired conversion to the diamine (I) has been achieved. The process of the reaction can be followed using conventional procedures, for example, by subjecting aliquots to infrared or nuclear magnetic resonance spectroscopy, or high pressure liquid chromatography.

The process of the invention can be represented schematically as follows wherein the aniline acid addition salt is the hydrochloride for purposes of exemplification:

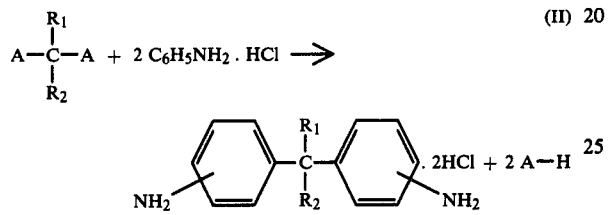

wherein $R_1$, $R_2$, and A are as hereinbefore defined.

The reaction product contains, as the principal components, the desired bis(aminophenyl)alkane, in the form of its dihydrochloride, and the substituted benzene compound (A-H) corresponding to the moiety A in the starting material (II). This mixture can be separated by conventional procedures, for example, by distillation under reduced pressure when the compound A-H, in most instances, can be removed as volatile overhead. The diamine salt which remains is purified by recrystallization, chromatography and like means before or after being converted to the free diamine by neutralization with aqueous alkali metal hydroxide or carbonate. Alternatively, the reaction mixture can be worked up by extracting the diamine salt in water, neutralizing the aqueous extract and recovering the free diamine by solvent extraction.

The above reaction of the compound (II) and the aniline acid addition salt can be carried out equally satisfactorily in the presence or absence of an inert solvent. When no solvent is employed, the two reactants are intimately mixed in the solid form, advantageously after comminution, or in the molten state, and heated to the appropriate reaction temperature with appropriate agitation of the melted reactants. Optionally, the heating step can be carried out under reduced pressure whereby part, or the whole, of the compound A-H liberated in the reaction distills out of the reaction mixture and thereby facilitates the subsequent recovery of the desired bis(aminophenyl)alkane from the reaction mixture.

Alternatively, the process of the invention can be carried out in the presence of an inert organic solvent, i.e. an organic solvent which does not enter into reaction with any of the initial reactants or the reaction products, or interfere in any other way with the desired course of the reaction. Illustrative of inert organic solvents are dichlorobenzene, trichlorobenzene, tetralin, decalin, trichlorophenol, and the like. Advantageously, when an inert organic solvent is employed, the aniline acid addition is dispersed or dissolved in the inert organic solvent and the mixture is heated with appropriate agitation to the desired reaction temperature before adding thereto a solution of the compound (II) in the inert organic solvent. The progress of the reaction is then followed by routine analytical procedures, such as those described above. When the reaction is deemed complete, the resulting solution is cooled to room temperature (circa 20° C.) and extracted with water to recover the desired bis(aminophenyl)alkane (I) as its acid addition salt in aqueous solution. The free diamine can then be liberated, if desired, by neutralization with aqueous alkali and isolated by extraction with an organic solvent.

The proportions of the reactants, namely the compound (II) and the aniline acid addition salt, employed in the process of the invention are so chosen that there are at least two molar proportions of aniline salt per mole of the compound (II). Preferably the proportions of the reactants are such that there are from 4 moles to 12 moles of aniline salt per mole of the compound (II).

It is found the di(aminophenyl)alkane (I) produced in accordance with the process of the invention is almost exclusively in the form of the 4,4'-isomer, i.e. the product is almost exclusively the bis(4-aminophenyl)alkane. The yield of the desired diamine (I) is generally in excess of about 90 percent thereby representing a dramatic increase in yield over the processes hitherto employed in the art.

A further advantage of the process of the present invention lies in the fact that the compound A-H which is produced as a by-product of the main reaction can be re-used in the production of further amounts of the starting compound (II) which latter can be employed in a subsequent run in accordance with the process of the invention. Thus, the starting material (II) is conveniently prepared by condensing the appropriate compound A-H wherein A is as hereinbefore defined, or a mixture of two different such compounds, with the appropriate alkanone $R_1$-CO-$R_2$, wherein $R_1$ and $R_2$ are as herebefore defined. The condensation is readily effected by bringing the reactants together, in at least stoichiometric proportions (2 moles of compound A-H to 1 mole of ketone) and preferably with the compound A-H in excess, in the presence of hydrogen chloride as the catalyst under conditions commonly employed in the preparation of Bisphenol-A and related compounds. A particularly convenient procedure for effecting the above condensation is that described in U.S. Pat. No. 4,052,466 for the preparation of Bisphenol A by condensing acetone and phenol in the presence of resorcinol or like polyhydric phenols or the ethers thereof and, optionally, thioglycolic acid as cocatalyst with hydrogen chloride.

Thus, by re-utilizing the compound A-H generated as by-product in the process of the invention, in the preparation of further starting material (II) for the process of the invention, it is possible to achieve economy in raw material costs and also achieve a semi-continuous process of operation.

The starting compounds A-H wherein A represents the group

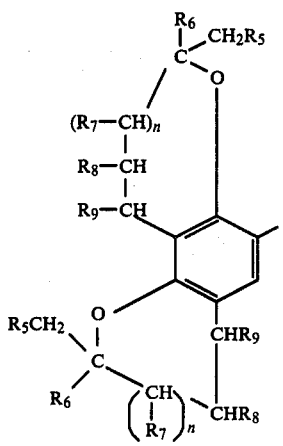

wherein $R_5$, $R_6$, $R_7$, $R_8$, $R_9$ and n have the significance hereinbefore defined are prepared advantageously by condensation of resorcinol with the appropriate diene

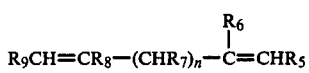

wherein $R_5$, $R_6$, $R_7$, $R_8$, $R_9$ and n have the significance hereinbefore defined. The condensation is carried out conveniently in the presence of boron trifluoride (advantageously in the form of its etherate) and an appropriate solvent such as glacial acetic acid. The condensation proceeds readily and it is generally unnecessary to provide any external heat to initiate the reaction or to maintain and complete it. Indeed, the reaction is mildly exothermic and it is sometimes necessary to provide external cooling to maintain the reaction rate within desired limits. The desired product is readily isolated from the reaction mixture and purified by conventional techniques, for example by diluting the reaction product with water and isolating the organic materials by extraction in an appropriate organic solvent. The product so isolated can be purified by distillation, chromatography and like techniques conventional in the art.

The starting compounds A-H wherein A represents the group

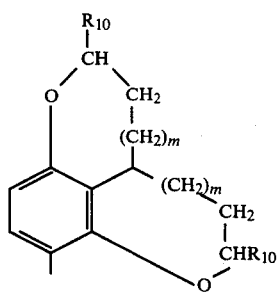

wherein $R_{10}$ and m have the significance hereinbefore defined can be prepared conveniently using the reaction shown schematically below:

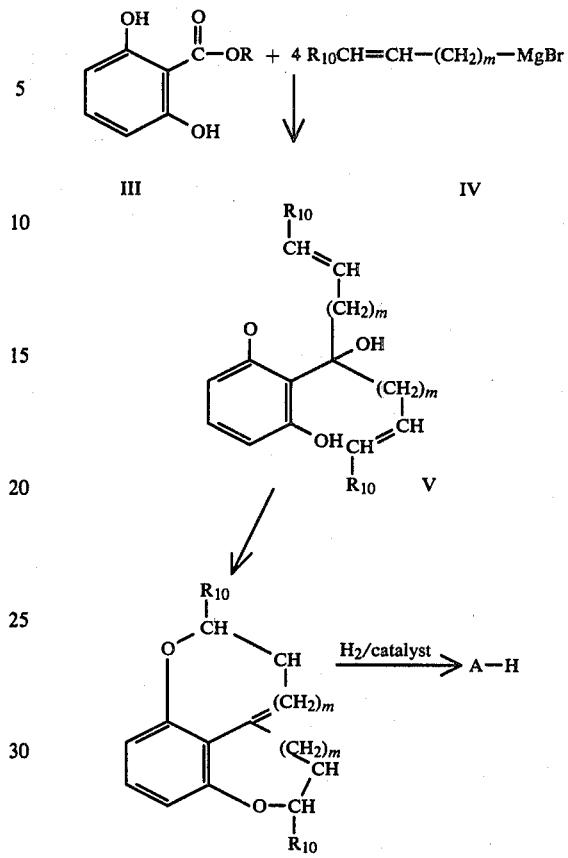

wherein R is lower alkyl, $R_{10}$ and m have the significance above defined. In the initial step the 2,6-dihydroxybenzoate (III) is subjected to Grignard reaction using the Grignard reagent (IV) to form the intermediate carbinol (V) which is then subjected to dehydration and cyclization under acidic conditions. In the final step the double bond in the cyclic ether so obtained is reduced by catalytic hydrogenation using conventional procedures.

The following examples describe the manner and process of making and using the invention and set forth the best mode contemplated by the inventor of carrying out the invention but are not to be construed as limiting.

EXAMPLE 1

A. Preparation of 2,2-bis(2,4-dimethoxyphenyl)propane.

A mixture of 199 g. (1.44 moles) of 1,3-dimethoxybenzene, 6.96 g. (0.12 mole) of acetone, 0.264 g. of resorcinol and 0.11 g. of thioglycolic acid was stirred and maintained at 27 to 30° C. while a stream of dry hydrogen chloride was bubbled into the mixture over a period of 5.5 hours. A total of 8.65 g. of hydrogen chloride was absorbed during this period. A small aqueous layer formed in the reaction product and was separated from the organic layer. The latter was diluted with 250 ml. of ether and washed successively with 25 ml. of aqueous 5 N sodium hydroxide solution and with two portions (25 ml.) of water before being dried over anhydrous sodium sulfate. The dried solution was evaporated to remove the ether and the residue was distilled under reduced pressure up to 130° C. at 0.1 mm. The distillate (170.8 g.) recovered was 1,3-dimethoxybenzene. The residue (31.2 g.) was crude 2,2-bis(2,4-dimethoxyphenyl)propane respresenting a 97 percent yield based on 1,3-dimethoxybenzene consumed. A portion (14.3 g.) of this crude material was distilled in vacuo to obtain 12.9 g. of 2,2-bis(2,4-dimethoxyphenyl)propane having a boiling point of 170° to 190° C. at 0.04 mm. This material crystallized to a solid which after being recrystallized from petroleum ether had a melting point of 65°–67° C.

B. Preparation of 2,2-bis(4-aminophenyl)propane.

A suspension of 41.6 g. (0.32 mole) of aniline hydrochloride in 70 ml. of 1,2,4-trichlorobenzene was stirred under nitrogen and heated rapidly to 195° to 200° C. at which temperature the aniline hydrochloride had melted. To this mixture was added, with rapid stirring, a solution of 12.64 g. (0.04 mole) of 2,2-bis(2,4-dimethoxyphenyl)propane (prepared as described above) in 30 ml. of 1,2,4-trichlorobenzene. The temperature of the reaction mixture was maintained at 194° to 195° C. during the addition (over a period of 10 minutes) and was maintained thereafter at the same level for a further 20 minutes. The product so obtained was cooled to room temperature, diluted with 150 ml. of chloroform, and extracted with 150 ml. of water. The aqueous phase was separated and washed with two portions (100 ml.) of chloroform. The chloroform extracts were combined and washed with 1 N hydrochloric acid and then with water. The acid and water washings were combined with the above aqueous phase. The combined aqueous phases were made alkaline by addition of aqueous 5 N sodium hydroxide and extracted with chloroform (3 portions each of 100 ml.). The chloroform extracts were dried over anhydrous magnesium sulfate and the dried solution was evaporated to dryness. The residue was distilled in vacuo to remove 22.3 g. of aniline and leave a residue of 7.63 g. which was shown by high pressure liquid chromatography to contain 96.6 percent of 2,2-bis(4-aminophenyl)propane.

The organic layer recovered from the reaction product was combined with the chloroform washings of the aqueous layer separated from the reaction product and the combined solution was dried over anhydrous magnesium sulfate and the chloroform was evaporated therefrom. The residue was distilled in vacuo to give 147.9 g. of distillate which was a mixture of trichlorobenzene and 1,3-dimethoxybenzene. The undistilled residue was found by high pressure liquid chromatography to contain 1.36 g. (0.0043 mole) of unreacted 2,2-bis(2,4-dimethoxyphenyl)propane.

The conversion of 2,2-bis(2,4-dimethoxyphenyl)propane to 2,2-bis(4-aminophenyl)propane was therefore 89.2 percent and the yield of the latter product was 91.3 percent.

EXAMPLE 2

A mixture of 6.32 g. (0.02 mole) of powdered 2,2-bis(2,4-dimethoxyphenyl)propane and 20.8 g. (0.16 mole) of powdered aniline hydrochloride was heated with stirring under a pressure of 220 mm. of mercury. The reaction mixture melted at 185° C. (6 minutes from beginning of heating) and the reaction was heated at 185° C. to 195° C. for 4 minutes during which time 2.2 g. of 1,3-dimethoxybenzene and some aniline hydrochloride distilled. The reaction mixture was then cooled rapidly and worked up as described in Example 1, part B for the reaction product described in Example 1. There was thus obtained 3.55 g. (0.0157 mole) of 2,2-bis(4-aminophenyl)propane, 0.02 g. of recovered 2,2-bis(2,4-dimethoxyphenyl)propane, and 0.66 g. of 2-(4-aminophenyl)-2-(2,4-dimethoxyphenyl)propane. The conversion was 86.8 percent and the yield of desired product 90.4 percent.

EXAMPLE 3

The procedure of Example 2 was repeated using double the quantities of starting materials and carrying out the reaction at atmospheric pressure. The heating time at 180° C. to 195° C. was extended to 6 minutes before the product was cooled to room temperature and worked up as described in Example 2. There was thus obtained 7.25 g. of 2,2-di(4-aminophenyl)propane, 21.55 g. of recovered aniline and 9.50 g. of 1,3-dimethoxybenzene.

EXAMPLE 4

A. Preparation of 2,2-bis(2,4-diethoxyphenyl)propane.

A mixture of 9.96 g. (0.06 mole) of 1,3-diethoxybenzene, 0.87 g. (0.015 mole) of acetone, 0.01 g. of resorcinol and 0.01 g. of thioglycolic acid was stirred while dry hydrogen chloride was bubbled in until the mixture was saturated. The resulting mixture was stirred at room temperature (circa 25° C.) for 65 hr. At the end of this time the reaction mixture was diluted with ether and the ethereal solution was washed successively with water, 1 N aqueous sodium hydroxide solution, and then again with water. The ether solution was then dried over anhydrous magnesium sulfate and the dried solution was evaporated to dryness. The residue was distilled under reduced pressure to yield a first fraction (1,3-diethoxybenzene) boiling up to 80° C. at 0.5 mm. followed by 4.25 g. of 2,2-bis(2,4-diethoxyphenyl)propane boiling point 180° to 190° C. at 0.5 mm. The latter material solidified on cooling and was recrystallized from petroleum ether to give 2.4 g. of colorless crystals having a melting point of 76° to 78° C.

B. Preparation of 2,2-bis(4-aminophenyl)propane.

Using the procedure described in Example 3 but employing 1.3 g. (3.5 mmole) of 2,2-bis(2,4-diethoxyphenyl)propane (prepared as described above) and 4.55 g. (35.0 mmole) of aniline hydrochloride, there was obtained 0.71 g. of 2,2-bis(4-aminophenyl)propane.

EXAMPLE 5

A. Preparation of 2,2,6,6-tetramethyldihydropyran[2,3-f]chroman

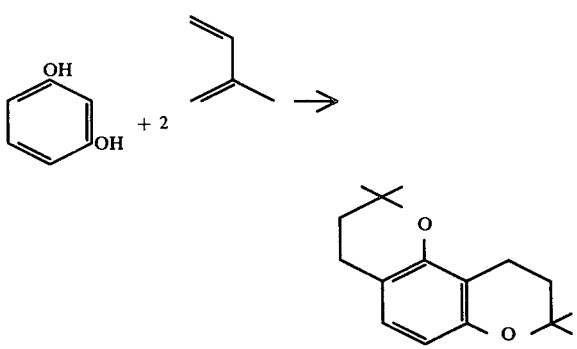

A solution of 44 g. (0.4 mole) of resorcinol and 54.4 g. (0.8 mole) of isoprene in 100 ml. of glacial acetic acid was added dropwise with stirring to a solution of 4.98 g. (0.035 mole) of boron trifluoride etherate in 100 ml. of glacial acetic acid. The rate of addition was such as to maintain the temperature of the reaction mixture at 30°–40° C. After the addition was complete (ca. 5 hr.), the reaction mixture was subjected to stirring at the same temperature for a further 20 minutes. At the end of this time the reaction product was extracted between 1 liter of water and 350 ml. of chloroform. The organic layer was separated and washed with dilute aqueous sodium hydroxide before being dried over anhydrous magnesium sulfate. The dried solution was evaporated to remove chloroform and the residue was distilled under reduced pressure to obtain 35.2 g. of product having a boiling point of 105° to 130° C. at 0.05 mm. of mercury. This product was subjected to chromatography using a silica gel dry column to obtain 2,2,6,6-tetramethyldihydropyran-[2,3-f]chroman in the form of a light yellow oil having a boiling point of 92° to 98° C. at 0.02 mm. of mercury.

| Calculated for $C_{16}H_{22}O_2$: | C, 78.15 | 8.01; | H, 9.29 | 9.00 |
|---|---|---|---|---|
| Found : C, | 78.33 | ; | H, 9.10 | |

B. Condensation of acetone and 2,2,6,6-tetramethyldihydropyrano[2,3-f]chroman

A solution of 2.46 g. (10 mmole) of 2,2,6,6-tetramethyldihydropyrano[2,3-f]chroman in 0.29 g. (5.0 mmole) of acetone was stirred, with cooling in a water bath, while dry hydrogen chloride was bubbled in slowly. A rapid reaction took place and, twenty minutes after the first introduction of the hydrogen chloride, the mixture became a light reddish brown solid. The latter was dissolved in ether and the ethereal solution was washed with N sodium hydroxide solution and then with water before being dried over anhydrous magnesium sulfate. The dried solution was evaporated to dryness and the residual white solid (2.75 g.) was recrystallized from a mixture of ethyl alcohol and carbon tetrachloride. There was thus obtained 10,10-isopropylidenebis(2,2,6,6-tetramethyldihydropyran[2,3-f]chroman) in the form of colorless crystals having a melting point of 198°–200° C. and corresponding to the formula

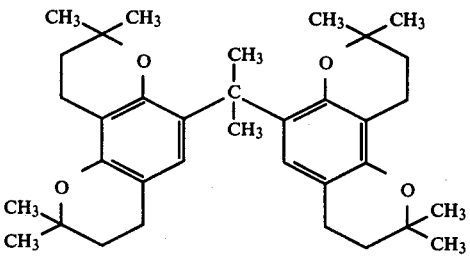

Calculated for $C_{35}H_{48}O_4$: C, 78.90; H, 9.08; Found: C, 78.57; H, 8.80.

C. Preparation of 2,2-bis(4-aminophenyl)propane

A mixture of B 1.064 g. (2 mmole) of 10,10-isopropylidenebis(2,2,6,6-tetramethyldihydropyran[2,3-f]chroman) (prepared as described in B above) and 2.08 g. (16 mmole) of aniline hydrochloride was heated in an oil bath. The mixture melted at 196° C. and was then stirred rapidly at 196°–205° C. for 25 minutes before being cooled to room temperature. The resulting product was extracted between water and chloroform. The chloroform extracts were found (by high pressure liquid chromatography) to contain 0.70 mmole of unreacted starting material (isopropylidene compound) and 1.3 mmole of 2,2,6,6-tetramethyldihydropyran[2,3-f]chroman together with a small amount of free aniline. The aqueous extract was neutralized with N sodium hydroxide solution and the organic material so generated was extracted with chloroform. The chloroform extracted was dried over anhydrous magnesium sulfate and evaporated to dryness and the residue was subjected to distillation up to a temperature of 130° C. at 0.02 mm of mercury to remove free aniline. The residue of the distillation was 0.268 g. (91.2 percent yield based on isopropylidene starting material converted) of 2,2-bis(4-aminophenyl)propane.

I claim:

1. A process for the preparation of a bis(aminophenyl)alkane having the formula

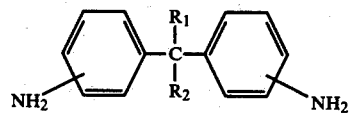

wherein $R_1$ and $R_2$, taken individually, represent methyl and lower-alkyl, respectively, and $R_1$ and $R_2$ taken together with the C atom to which they are attached represent the residue of a 1,1-cycloalkylidene group having from 5 to 7 ring carbon atoms, inclusive; which process comprises reacting (a) the appropriately substituted bis(phenyl)alkane having the formula:

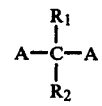

wherein $R_1$ and $R_2$ have the significance defined above and A is a member selected from the class consisting of

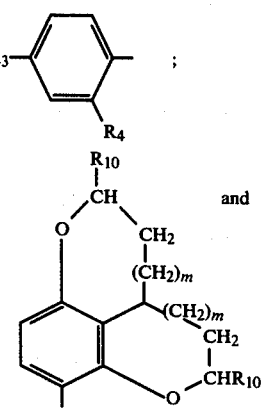

-continued

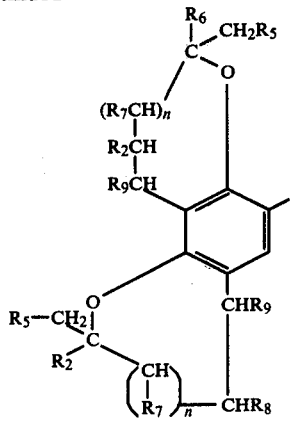

wherein $R_3$ and $R_4$ each represent lower alkoxy; $R_5$, $R_6$, $R_7$, $R_8$, $R_9$ and $R_{10}$ are each independently selected from the group consisting of hydrogen and lower-alkyl; and n and m are integers from 0 to 1; with (b) at least 2 moles, per mole of said bis-(phenyl)alkane, of an aniline acid addition salt at a temperature in the range of 100° to 250° C.

2. The process of claim 1 wherein said substituted bis(phenyl)alkane is 2,2-bis(2,4-dimethoxyphenyl)propane and the aniline acid addition salt is aniline hydrochloride whereby there is obtained 2,2-bis(4-aminophenyl)propane in the form of its dihydrochloride.

3. The process of claim 1 wherein said bis(phenyl)alkane is 2,2-bis(2,4-diethoxyphenyl)propane and the aniline acid addition salt is aniline hydrochloride whereby there is obtained 2,2-bis(4-aminophenyl)propane in the form of its dihydrochloride.

4. The process of claim 1 wherein the bis(phenyl)alkane is 10,10-isopropylidenebis(2,2,6,6-tetramethyldihydropyran[2,3-f]chroman).

5. The process of claim 1 wherein said reaction is carried out in the presence of an inert organic solvent.

6. The process of claim 1 wherein said reaction is carried out by heating the reactants in the absence of an inert organic solvent.

7. The process of claims 2 or 3 wherein said reaction is carried out at a pressure less than atmospheric and the 1,3-di-lower-alkoxybenzene by-product is recovered overhead.

8. A process which comprises heating together a 2,2-bis(2,4-di-loweralkoxyphenyl)propane and from 2 mole to 14 mole, per mole of the former, of aniline hydrochloride at a temperature of 100° C. to 250° C. whereby there is obtained 2,2-bis(4-aminophenyl)-propane in the form of its dihydrochloride.

9. The process of claim 8 wherein the heating is carried out in the presence of an inert orgaic solvent.

10. The process of claim 8 wherein the heating is carried out in the absence of an inert solvent.

11. The process of claim 8 wherein said reaction is carried out at a pressure less than atmospheric and the 1,3-di-lower-alkoxybenzene by-product is recovered overhead.

12. A process which comprises heating together 2,2-bis(2,4-dimethoxyphenyl)propane and from 2 mole to 14 mole, per mole of the former, of aniline hydrochloride at a temperature of 100° C. to 250° C. whereby there is obtained 2,2-bis(4-aminophenyl)-propane in the form of its dihydrochloride.

13. The process of claim 12 wherein the heating is carried out in the presence of an inert organic solvent.

14. The process of claim 12 wherein the heating is carried out in the absence of an inert solvent.

15. The process of claim 12 wherein said reaction is carried out at a pressure less than atmospheric and the 2,4-dimethoxybenzene by-product is recovered overhead.

* * * * *

UNITED STATES PATENT OFFICE
CERTIFICATE OF CORRECTION

Patent No. 4,177,211    Dated December 4, 1979

Inventor(s) Kwok K. Sun

It is certified that error appears in the above-identified patent and that said Letters Patent are hereby corrected as shown below:

Column 1, lines 64-68:    Should read:

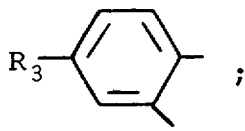    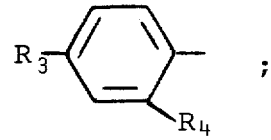

Column 6, Formula V, left-hand portion - Should read:

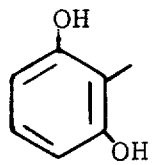

Column 8, line 44:    Should read:

0.71 g. of 2,2-bis(4-amino-phenyl)propane.

0.71 g. [90% yield based on 2,2-bis(2,4-diethoxyphenyl)-propane] of 2,2-bis(4-aminophenyl)propane.

Column 9, line 19:    Should read:

C, 8.01;    C, 78.01;

UNITED STATES PATENT OFFICE
CERTIFICATE OF CORRECTION

Patent No. 4,177,211      Dated December 4, 1979

Inventor(s) Kwok K. Sun

It is certified that error appears in the above-identified patent and that said Letters Patent are hereby corrected as shown below:

Column 9, line 59:

of B 1.064 g.

Should read:

of 1.064 g.

Column 11, Claim 1, Lines 1-17.

The formula should read:

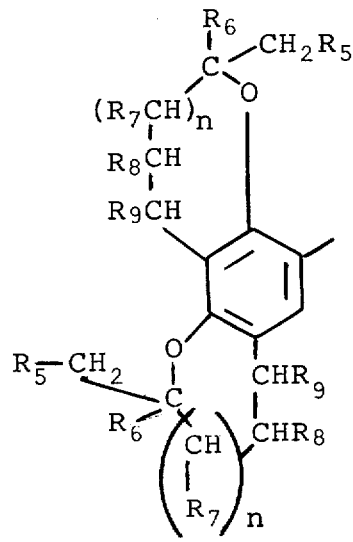

Signed and Sealed this

Sixth Day of May 1980

[SEAL]

Attest:

SIDNEY A. DIAMOND

Attesting Officer     Commissioner of Patents and Trademarks